United States Patent
Tate et al.

(10) Patent No.: US 9,791,424 B2
(45) Date of Patent: Oct. 17, 2017

(54) USE OF WINDOWED MASS SPECTROMETRY DATA FOR RETENTION TIME DETERMINATION OR CONFIRMATION

(71) Applicant: DH Technologies Development Pte. Ltd., Singapore (SG)

(72) Inventors: Stephen A. Tate, Barrie (CA); Lyle Burton, Woodbridge (CA)

(73) Assignee: DH Technologies Development Pte. Ltd., Singapore (SG)

( * ) Notice: Subject to any disclaimer, the term of this patent is extended or adjusted under 35 U.S.C. 154(b) by 17 days.

(21) Appl. No.: 15/098,197

(22) Filed: Apr. 13, 2016

(65) Prior Publication Data

US 2016/0231295 A1    Aug. 11, 2016

Related U.S. Application Data

(63) Continuation of application No. 14/368,874, filed as application No. PCT/IB2012/002723 on Dec. 15, 2012, now Pat. No. 9,343,276.

(Continued)

(51) Int. Cl.
*G01N 30/86* (2006.01)
*H01J 49/00* (2006.01)
(Continued)

(52) U.S. Cl.
CPC ......... *G01N 30/8634* (2013.01); *G01N 30/72* (2013.01); *G06F 19/703* (2013.01);
(Continued)

(58) Field of Classification Search
CPC ............... H01J 49/0036; H01J 49/0045; H01J 49/4265; G01N 27/62
See application file for complete search history.

(56) References Cited

U.S. PATENT DOCUMENTS 5,298,746 A    3/1994   Franzen et al.
7,473,892 B2 *  1/2009   Sano .................. G01N 33/6848
                                              250/281

(Continued)

FOREIGN PATENT DOCUMENTS

JP      05-258713 A    10/1993
JP      08-017391 A     1/1996

OTHER PUBLICATIONS

International Search Report and Written Opinion for PCT/IB2012/002723, dated May 16, 2013.

*Primary Examiner* — David E Smith
*Assistant Examiner* — Hsien Tsai
(74) *Attorney, Agent, or Firm* — John R. Kasha; Kelly L. Kasha; Kasha Law LLC

(57) ABSTRACT

A scan of a separating sample is received by a mass spectrometer at each interval of a plurality of intervals. The spectrometer performs at each interval one or more mass spectrometry scans. The scans have one or more sequential mass window widths in order to span an entire mass range at each interval and produce a collection of spectra for the entire mass range for the plurality of intervals. One or more peaks at one or more different intervals in the collection of spectra are identified for a fragment ion. A mass spectrum of the entire mass range is retrieved for each interval of each peak. Values for one or more ion characteristics of a mass-to-charge ratio peak in the mass spectrum corresponding to each peak are compared to one or more known values for the fragment ion. Each peak is scored based on the comparison.

20 Claims, 4 Drawing Sheets

Related U.S. Application Data

(60) Provisional application No. 61/581,423, filed on Dec. 29, 2011.

(51) Int. Cl.
*H01J 49/26* (2006.01)
*G06F 19/00* (2011.01)
*G01N 30/72* (2006.01)

(52) U.S. Cl.
CPC ........ *H01J 49/004* (2013.01); *H01J 49/0031* (2013.01); *H01J 49/0036* (2013.01); *H01J 49/0045* (2013.01); *H01J 49/26* (2013.01)

(56) References Cited

U.S. PATENT DOCUMENTS

| | | |
|---|---|---|
| 2004/0217272 A1 | 11/2004 | Horning et al. |
| 2007/0096021 A1 | 5/2007 | LeBlanc et al. |
| 2010/0213368 A1* | 8/2010 | Wang .................. H01J 49/0036 250/282 |

* cited by examiner

USE OF WINDOWED MASS SPECTROMETRY DATA FOR RETENTION TIME DETERMINATION OR CONFIRMATION

CROSS REFERENCE TO RELATED APPLICATION

This application is a continuation of U.S. patent application Ser. No. 14/368,874, filed Jun. 26, 2014, filed as Application No. PCT/IB2012/002723 on Dec. 15, 2012, which claims the benefit of U.S. Provisional Patent Application Ser. No. 61/581,423, filed Dec. 29, 2011, the disclosures of which are incorporated by reference herein in their entireties.

INTRODUCTION

Mass spectrometers are often coupled with chromatography or other separation systems in order to identify and characterize eluting compounds of interest from a sample. In such a coupled system, the eluting solvent is ionized and a series of mass spectra are obtained from the eluting solvent at specified time intervals. These time intervals range from, for example, 1 second to 100 minutes or greater. The series of mass spectra form a chromatogram.

Peaks found in the chromatogram are used to identify or characterize a compound of interest in the sample. In complex mixtures, however, interference with other peaks having the same mass-to-charge ratio (m/z) can make it difficult to determine a peak representing a compound of interest. In some cases, no information is available regarding the expected retention time of the compound of interest. In other cases, an approximate retention time of the compound of interest may be known. However, even in this latter case, the exact peak of the compound of interest can be ambiguous if the sample is complex or if there is more than a small amount of retention time variation between samples. As a result, it is often difficult to identify or characterize the compound of interest in these cases.

BRIEF DESCRIPTION OF THE DRAWINGS

The skilled artisan will understand that the drawings, described below, are for illustration purposes only. The drawings are not intended to limit the scope of the present teachings in any way.

Figure 1:
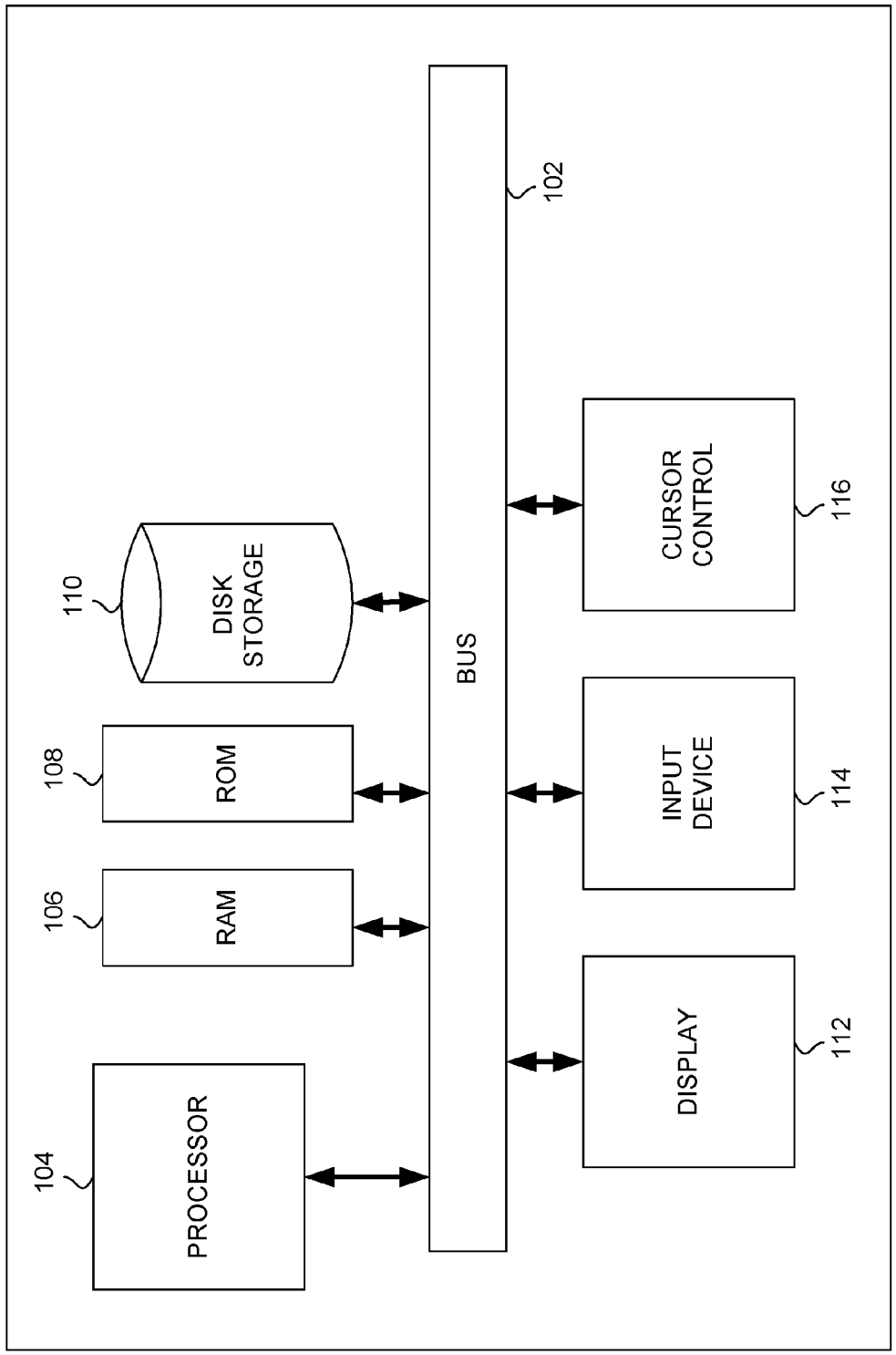
FIG. 1 is a block diagram that illustrates a computer system, in accordance with various embodiments.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Scoring Peaks of a Collection of Spectra

As described above, mass spectrometers coupled with separation systems are used to identify and characterize compounds of interest separating from a sample. The separating sample is ionized and a series of mass spectra for the sample are obtained at specified intervals. In chromatographic systems, the series of spectra collected over time is called a chromatogram, for example. For any separation device or system, the series of spectra collected over a number of intervals of a separation system is referred to herein as a collection of spectra.

Peaks found in the collection of spectra are used to identify or characterize a compound of interest in the sample. However, in complex samples, interfering peaks and approximate or no information regarding the retention time of the compound of interest can make it difficult to identify or characterize the compound of interest.

In traditional separation coupled mass spectrometry systems, a fragment ion of a known compound of interest is selected for analysis. A mass spectrometry scan is then performed at each interval of the separation for a mass range that includes the fragment ion. The intensity of the fragment ion found in each spectrometry scan is collected over time and analyzed as a collection of spectra, or an ion chromatogram (XIC), for example.

For a simple sample mixture, for example, a single peak representing the fragment ion is typically found in the XIC at the expected retention time of the known compound. For more complex mixtures, however, two or more peaks that represent the fragment ion are located at one or more additional time intervals in the collection of spectra in addition to the expected retention time of the compound of interest. In other words, an XIC for the fragment ion can have two or more peaks.

One traditional method of identifying compounds of interest in more complex mixtures has been to locate time intervals where two or more of the fragment ions of the known compound have peaks. This method is used in proteomics, for example, when a peptide of a known sequence is quantitated.

In a typical multiple reaction monitoring (MRM) method two or more MRM transitions are monitored, each corresponding to a different fragment of the peptide. If previous discovery data is available, these transitions are based on the largest fragments that are observed in the data. Otherwise these transitions are based on predicted y-ions, for example. The XIC is analyzed for these two or more MRM transitions. The time at which there is a peak for all transitions is used to characterize the compound of interest.

For complex samples, especially if the expected retention time is not known accurately, there can be ambiguity in the collection of spectra. For example, there can be more than one retention time or time interval for which there is a peak for each of the two or more MRM transitions.

Little additional information is available to address the ambiguity introduced by complex samples. In traditional separation coupled mass spectrometry systems, each mass spectrometry scan for each fragment ion at each time interval is typically performed using a narrow mass window width. As a result, the mass spectrum at a particular time interval for each fragment ion that is available after data acquisition can provide little additional insight.

In various embodiments, a separation coupled mass spectrometry system is used that performs mass spectrometry scans at each time interval using one or more sequential mass window widths in order to span an entire mass range. In other words, spectral information for an entire mass range can be obtained at each time interval in the separation. Recently developed high-resolution and high-throughput instruments allow a mass range to be accurately scanned within a time interval using multiple scans with adjacent or overlapping mass window widths. Results from the multiple scans can be pieced together to produce a spectrum for the entire mass range at each time interval. The collection of each spectrum at each time interval of the separation is a collection of spectra for the entire mass range. One exemplary method for using windowed mass spectrometry scans to scan an entire mass range is called sequential windowed acquisition through libraries (SWATH).

In various embodiments, the spectral information for an entire mass range collected using the windowed acquisition method is used to resolve the retention time ambiguity in complex mixtures. In other words, when a fragment ion is found to have two or more peaks in the collection of spectra at two or more different time intervals in the separation, a mass spectrum of the entire mass range at each of the different time intervals can be analyzed to determine the actual retention time. A variety of criteria can be used to analyze the mass spectra of the entire mass range. Based on these criteria each peak and/or time interval is scored. A retention time for the known compound is identified from the peak or peaks with the highest score or combined score.

Returning to the proteomics example, a complex sample can have two or more time intervals where there is a peak for each of the two or more extracted parent/daughter ion combinations. In other words, a peak group representing the peptide can be found at two or more time intervals. In various embodiments, the mass spectrum for each entire mass range that was collected for each of the two or more time intervals is examined.

If the mass accuracy for one or more of the expected masses is poor, for example, this is an indication that the peak in the collection of spectra does not correspond to the expected fragment of interest and this candidate can be eliminated or, in practice, can have its score reduced. This scoring can be based not just on the two or more initial expected masses, but on other expected sequence ions for the peptide. In many cases, peaks in the collection of spectra correspond to isotope peaks of other compounds, or to peaks with an incorrect charge state (and hence also unrelated to the compound of interest). For the traditional MRM method there is no way to detect this situation, but when the windowed data acquisition method is used, this situation can be detected and the corresponding candidate can be ranked more poorly as a result.

This technique is powerful for peptides since likely sequence ions can be predicted, but it is also very applicable to small molecules provided that an initial fragment spectrum is available. In this case one would probably identify the largest observed fragments collection of spectra, but perform scoring using any other significant observed fragments. One additional use of such peak group scoring can be to determine the most specific fragment mass or masses, not just for the initial masses identified in the collection of spectra, but also considering additional expected or predicted fragments. This is most useful when "discovery" data is not available so that theoretical peptide y-ions are used or when any such discovery data is acquired. If this is done for a sample known (or suspected) to contain the peptide of interest, the resulting optimized fragment masses can be used for subsequent processing (i.e., XIC calculation) for other samples.

Figure 2:
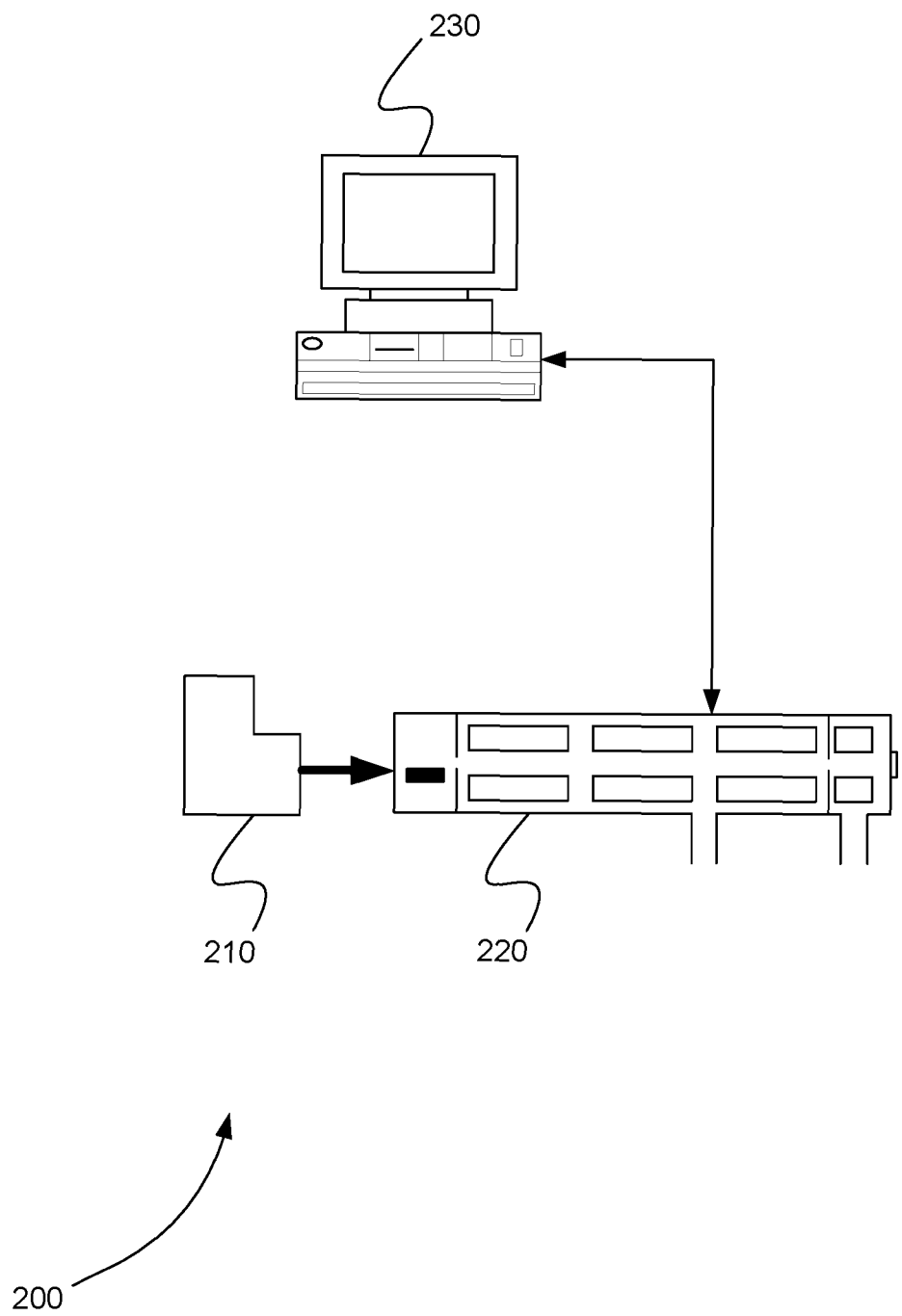
FIG. 2 is a schematic diagram showing a system for scoring peaks of a known compound of interest from a collection of spectra, in accordance with various embodiments.

Systems and Methods of Data Processing
Separation Coupled Mass Spectrometry System FIG. 2 is a schematic diagram showing a system 200 for scoring peaks of a known compound of interest from a collection of spectra, in accordance with various embodiments. System 200 includes separation device 210, mass spectrometer 220, and processor 230. Separation device 210 separates one or more compounds from a sample mixture. Separation device 210 can include, but is not limited to, an electrophoretic device, a chromatographic device, or a mobility device.

Mass spectrometer 220 is a tandem mass spectrometer, for example. Mass spectrometer 220 can include one or more physical mass analyzers that perform two or more mass analyses. A mass analyzer of a tandem mass spectrometer can include, but is not limited to, a time-of-flight (TOF), quadrupole, an ion trap, a linear ion trap, an orbitrap, a magnetic four-sector mass analyzer, a hybrid quadrupole time-of-flight (Q-TOF) mass analyzer, or a Fourier transform mass analyzer. Mass spectrometer 220 can include separate mass spectrometry stages or steps in space or time, respectively.

Mass spectrometer 220 performs at each interval of a plurality of intervals one or more mass spectrometry scans on the separating sample mixture. An interval can include, but is not limited to, a time interval or an interval of ion mobility. The one or more mass spectrometry scans have one or more sequential mass window widths in order to span an entire mass range at the interval. As a result, mass spectrometer 220 produces a collection of spectra for the entire mass range for the plurality of intervals. This collection of spectra is stored in a memory, for example.

Processor 230 is in communication with tandem mass spectrometer 220. Processor 230 can also be in communication with separation device 210. Processor 230 can be, but is not limited to, a computer, microprocessor, or any device capable of sending and receiving control signals and data to and from tandem mass spectrometer 220 and processing data.

Processor 230 receives the collection of spectra from mass spectrometer 220, for example. In various embodiments, processor 230 can receive the collection of spectra from a file stored in a memory. Processor 230 performs the following steps. In step 1, processor selects a fragment ion of a known compound. In step 2, processor 230 identifies for the fragment ion one or more peaks at one or more different intervals in the collection of spectra.

In step 3, processor 230 scores each peak of the one or more peaks. Processor 230 retrieves a mass spectrum of the entire mass range for each interval of each peak from the collection of spectra. Processor 230 compares values of one or more ion characteristics of a mass-to-charge ratio peak in the mass spectrum corresponding to each peak to one or more known values for the fragment ion. Finally, processor 230 bases the score of each peak on the results of the comparison.

In various embodiments, the one or more ion characteristics include, but are not limited to, charge state, isotopic state, mass accuracy, or one or more mass differences associated with a known fragmentation profile of the known compound.

In various embodiments, processor 230 further identifies a separation interval of the known compound based on scores of the one or more peaks. Processor 230 identifies a separation interval of the known compound as the interval of a peak of the one or more peaks with the highest score, for example. The separation interval can include, but is not limited to, a retention time in a chromatographic system or an ion mobility at which the compound of interest passes through an ion mobility system.

In various embodiments, processor 230 further performs steps 1-3 for one or more additional fragment ions of the known compound. As a result, processor 230 produces scores for each peak of two or more fragment ions of the known compound. Processor 230 identifies two or more different intervals where each fragment ion of the two or more fragment ions has a peak in the collection of spectra. Processor 230 combines scores of peaks from the two or more fragment ions at each of the two or more different intervals to produce a combined score for each of the two or more intervals. Finally, Processor 230 identifies an interval of the two or more different intervals with the highest score as a separation interval for the known compound.

In various embodiments, a mass spectrum of the entire mass range from the collection of spectra at the separation interval is used for quantitation of the known compound. Alternatively, a mass spectrum of the entire mass range from the collection of spectra at the separation interval is used to locate a modified form of the known compound, for example.

Mass Spectrometry Method

Figure 3:
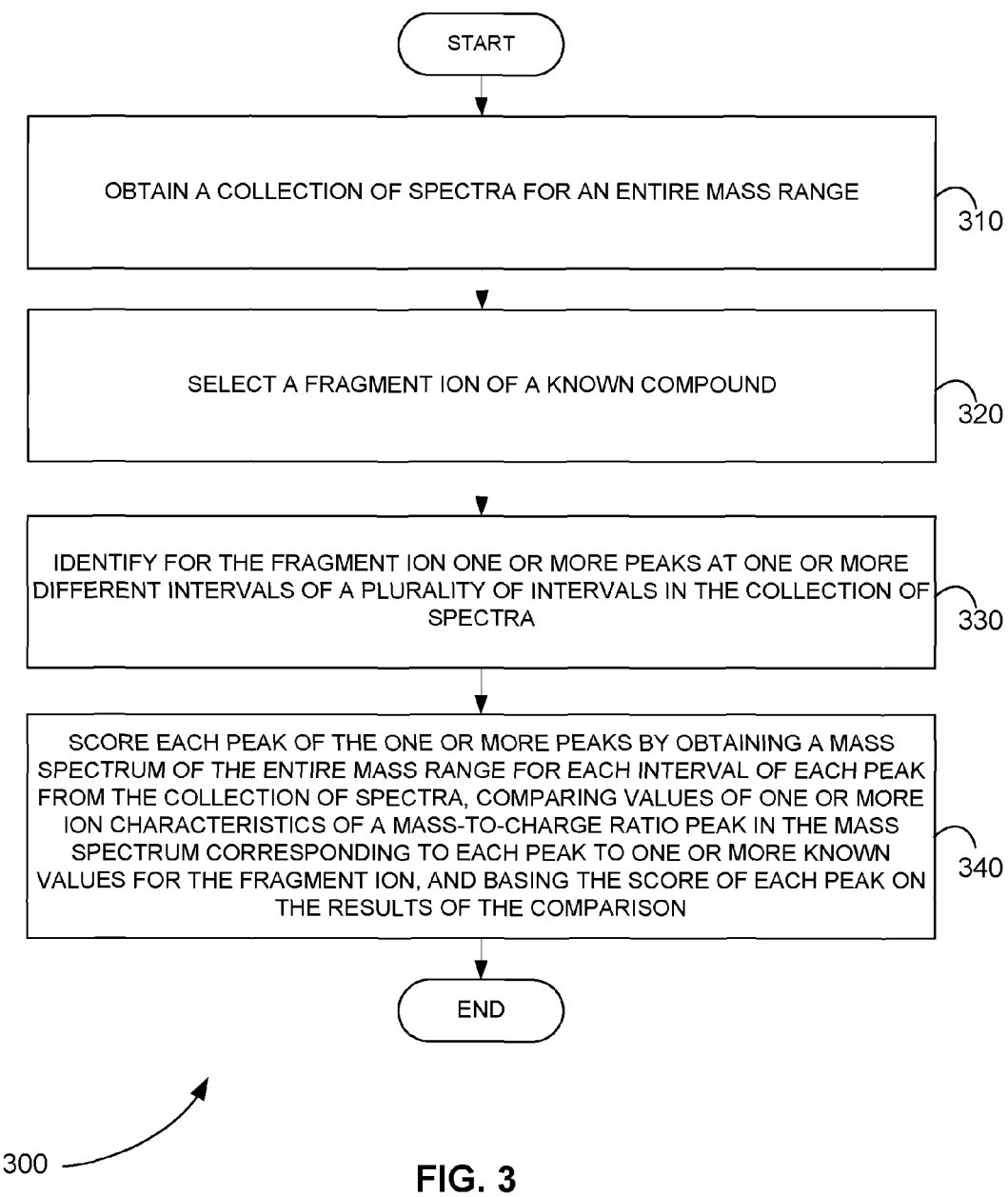
FIG. 3 is an exemplary flowchart showing a method for scoring peaks of a known compound of interest from a collection of spectra, in accordance with various embodiments.

FIG. 3 is an exemplary flowchart showing a method 300 for scoring peaks of a known compound of interest from a collection of spectra, in accordance with various embodiments.

In step 310 of method 300, a collection of spectra is obtained for an entire mass range. One or more compounds are separated from a sample mixture using a separation device. One or more mass spectrometry scans are performed on the separating sample mixture at each interval of a plurality of intervals using one or more sequential mass window widths in order to span the entire mass range. The collection of spectra for the entire mass range for the plurality of intervals is produced using a mass spectrometer. The collection of spectra is obtained directly from the mass spectrometer, or indirectly from a file that stores the results produced by the mass spectrometer.

In step 320, a fragment ion of a known compound is selected.

In step 330, for the fragment ion, one or more peaks at one or more different intervals of the plurality of intervals are identified in the collection of spectra.

In step 340, each peak of the one or more peaks is scored by obtaining a mass spectrum of the entire mass range for each interval of each peak from the collection of spectra, comparing values of one or more ion characteristics of a mass-to-charge ratio peak in the mass spectrum corresponding to each peak to one or more known values for the fragment ion, and basing the score of each peak on the results of the comparison.

Mass Spectrometry Computer Program Product

In various embodiments, a computer program product includes a non-transitory and tangible computer-readable storage medium whose contents include a program with instructions being executed on a processor so as to perform a method for scoring peaks of a known compound of interest from a collection of spectra. This method is performed by a system that includes one or more distinct software modules.

Figure 4:
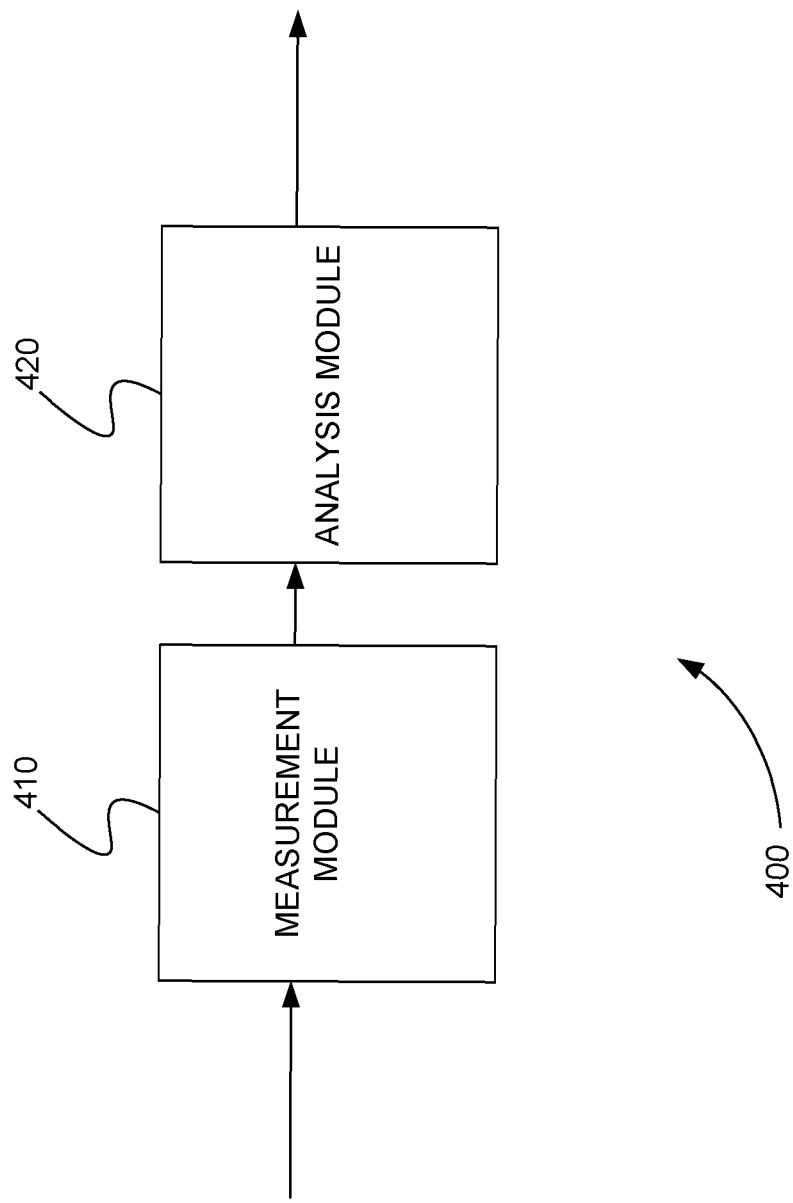
FIG. 4 is a schematic diagram of a system that includes one or more distinct software modules that perform a method for scoring peaks of a known compound of interest from a collection of spectra, in accordance with various embodiments.

FIG. 4 is a schematic diagram of a system 400 that includes one or more distinct software modules that perform a method for scoring peaks of a known compound of interest from a collection of spectra, in accordance with various embodiments. System 400 includes measurement module 410 and analysis module 420.

Measurement module 410 obtains a collection of spectra for an entire mass range. One or more compounds are separated from a sample mixture using a separation device. One or more mass spectrometry scans are performed on the separating sample mixture at each interval of a plurality of intervals using one or more sequential mass window widths in order to span the entire mass range. The collection of spectra for the entire mass range is produced for the plurality of intervals using a mass spectrometer.

Analysis module 420 selects a fragment ion of a known compound. Analysis module 420 identifies for the fragment ion one or more peaks at one or more different intervals of the plurality of intervals in the collection of spectra. Finally, analysis module 420 scores each peak of the one or more peaks. A mass spectrum of the entire mass range for each interval of each peak is obtained from the collection of spectra. Values of one or more ion characteristics of a mass-to-charge ratio peak in the mass spectrum corresponding to each peak are compared to one or more known values for the fragment ion. The score of each peak is based on the results of the comparison.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for scoring peaks of a known compound of interest from a collection of mass spectra, comprising:
   a separation device that separates one or more compounds from a sample mixture;
   a mass spectrometer that performs at each time interval of a plurality of time intervals one or more mass spectrometry scans on the separating sample mixture using one or more sequential mass window widths in order to span an entire mass range, producing a collection of mass spectra for the plurality of time intervals; and
   a processor that
   (a) selects a fragment ion of a known compound,
   (b) calculates an extracted ion chromatogram (XIC) for the fragment ion from the collection of mass spectra, wherein the XIC includes an intensity of the fragment ion for each time interval of the plurality of time intervals, and
   (c) if two or more XIC peaks corresponding to the fragment ion are found in the XIC at two or more different time intervals, scores each XIC peak in order to determine an actual retention time for the known compound by obtaining a mass spectrum of the entire mass range from the collection of mass spectra for each time interval and comparing values of one or more ion characteristics of a mass-to-charge ratio (m/z) peak of the fragment ion in each entire mass range mass spectrum to one or more known values for the fragment ion.

2. The system of claim 1, wherein the one or more ion characteristics comprise charge state.

3. The system of claim 1, wherein the one or more ion characteristics comprise isotopic state.

4. The system of claim 1, wherein the one or more ion characteristics comprise mass accuracy.

5. The system of claim 1, wherein the one or more ion characteristics comprise one or more mass differences associated with a known fragmentation profile of the known compound.

6. The system of claim 1, wherein the processor further identifies a separation time interval of the known compound based on scores of the two or more XIC peaks.

7. The system of claim 1, wherein the mass spectrometer performs one or more mass spectrometry scans by piecing together scan results of adjacent or overlapping sequential mass window widths.

8. The system of claim 6, wherein the processor identifies a separation time interval of the known compound as the time interval of an XIC peak of the two or more XIC peaks with the highest score.

9. The system of claim 1, wherein the processor further performs steps (a)-(c) for one or more additional fragment ions of the known compound producing scores for XIC peaks of two or more fragment ions of the known compound,
  identifies two or more different time intervals of the plurality of time intervals where each fragment ion of the two or more fragment ions has an XIC peak,
  combines scores of XIC peaks from the two or more fragment ions at each of the two or more different time intervals to produce a combined score for each of the two or more time intervals, and
  identifies a time interval of the two or more different time intervals with the highest score as a separation time interval for the known compound.

10. The system of claim 9, wherein a mass spectrum of the entire mass range from the collection of mass spectra at the separation time interval is used for quantitation of the known compound.

11. The system of claim 9, wherein a mass spectrum of the entire mass range from the collection of mass spectra at the separation time interval is used to locate a modified form of the known compound.

12. A method for scoring peaks of a known compound of interest from a collection of mass spectra, comprising:
  obtaining a collection of mass spectra for a plurality of time intervals, wherein one or more compounds are separated from a sample mixture using a separation device and wherein one or more mass spectrometry scans are performed on the separating sample mixture at each time interval of the plurality of time intervals using one or more sequential mass window widths in order to span the entire mass range producing a collection of mass spectra for the plurality of time intervals using a mass spectrometer;
  selecting a fragment ion of a known compound;
  calculating an extracted ion chromatogram (XIC) for the fragment ion from the collection of mass spectra, wherein the XIC includes an intensity of the fragment ion for each time interval of the plurality of time intervals; and
  if two or more XIC peaks corresponding to the fragment ion are found in the XIC two or more different time intervals, scores each XIC peak in order to determine an actual retention time for the known compound by obtaining a mass spectrum of the entire mass range from the collection of mass spectra for each of the two or more different time intervals, and comparing values of one or more ion characteristics of a mass-to-charge ratio (m/z) peak of the fragment ion in each entire mass range mass spectrum to one or more known values for the fragment ion.

13. The method of claim 12, wherein the one or more ion characteristics comprise charge state.

14. The method of claim 12, wherein the one or more ion characteristics comprise isotopic state.

15. The method of claim 12, wherein the one or more ion characteristics comprise mass accuracy.

16. The method of claim 12, wherein the one or more ion characteristics comprise one or more mass differences associated with a known fragmentation profile of the known compound.

17. The method of claim 12, further comprising identifying a separation time interval of the known compound based on scores of the two or more XIC peaks.

18. The method of claim 12, wherein the one or more mass spectrometry scans are performed on the separating sample mixture by piecing together scan results of adjacent or overlapping sequential mass window widths.

19. The method of claim 17, wherein a separation time interval of the known compound is identified as the time interval of an XIC peak of the two or more XIC peaks with the highest score.

20. A computer program product, comprising a non-transitory and tangible computer-readable storage medium whose contents include a program with instructions being executed on a processor so as to perform a method for scoring peaks of a known compound of interest from a collection of spectra, the method comprising:
  providing a system, wherein the system comprises one or more distinct software modules, and wherein the distinct software modules comprise a measurement module and an analysis module;
  obtaining a collection of mass spectra for a plurality of time intervals using the measurement module, wherein one or more compounds are separated from a sample mixture using a separation device and wherein one or more mass spectrometry scans are performed on the separating sample mixture at each time interval of the plurality of time intervals using one or more sequential mass window widths in order to span the entire mass range producing a collection of mass spectra for the plurality of time intervals using a mass spectrometer;
  selecting a fragment ion of a known compound using the analysis module;
  calculating an extracted ion chromatogram (XIC) for the fragment ion from the collection of mass spectra, wherein the XIC includes an intensity of the fragment ion for each time interval of the plurality of time intervals using the analysis module; and
  if two or more XIC peaks corresponding to the fragment ion are found in the XIC at two or more different time intervals, scores each XIC peak in order to determine an actual retention time for the known compound by obtaining a mass spectrum of the entire mass range from the collection of mass spectra for each of the two or more different time intervals, and comparing values of one or more ion characteristics of a mass-to-charge ratio (m/z) peak of the fragment ion in each entire mass range mass spectrum to one or more known values for the fragment ion.

\* \* \* \* \*